US007553847B2

(12) United States Patent
Clary et al.

(10) Patent No.: US 7,553,847 B2
(45) Date of Patent: Jun. 30, 2009

(54) USE OF PAGOCLONE FOR THE TREATMENT OF SOCIAL ANXIETY DISORDER

(75) Inventors: Cathryn M. Clary, New York, NY (US); Jeroen Van Beek, Ridgefield, CT (US); Perry S. Eisman, Southamton, NY (US); Sean Donevan, Dexter, MI (US); Atul Pande, East Lyme, CT (US); Richard Kavoussi, Ann Arbor, MI (US); Lyou-Fu Ma, Ann Arbor, MI (US)

(73) Assignee: Indevus Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 11/352,286

(22) Filed: Feb. 13, 2006

(65) Prior Publication Data

US 2006/0128746 A1 Jun. 15, 2006

Related U.S. Application Data

(63) Continuation of application No. 10/133,471, filed on Apr. 25, 2002, now Pat. No. 7,026,332.

(60) Provisional application No. 60/287,545, filed on Apr. 30, 2001.

(51) Int. Cl.
*A61K 31/4745* (2006.01)

(52) U.S. Cl. .................................................. 514/300

(58) Field of Classification Search ........................ None
See application file for complete search history.

(56) References Cited

U.S. PATENT DOCUMENTS

| 5,494,915 A | 2/1996 | Barreau et al. |
| 4,960,915 A | 3/1996 | Bourzat et al. |
| 5,498,716 A | 3/1996 | Comte et al. |
| 2003/0092719 A1 | 5/2003 | Day et al. |

FOREIGN PATENT DOCUMENTS

| GB | 2305859 A | | 4/1997 |
| WO | WO 93/01187 A1 | | 1/1993 |
| WO | WO 93/01189 A1 | | 1/1993 |
| WO | WO 93/01198 A1 | | 1/1993 |
| WO | WO 93/05041 A1 | | 3/1993 |
| WO | WO 93/11125 A1 | | 6/1993 |
| WO | WO 94/05663 A1 | | 3/1994 |
| WO | 99/63933 | * | 12/1999 |
| WO | WO 01/08670 A2 | | 2/2001 |

OTHER PUBLICATIONS

Van Ameringen et al., Expert Opinion on Investigative Drugs, 9(10) (2000), pp. 2215-2231.*
Pagoclone citation (entered in Registry file May 10, 1991).*
Doctor's Guide to the Internet, located at http://www.docguide.com (Nov. 20, 1997).*
Dunner, D.L., Depression and Anxiety, (Mar. 2001), 13(2), pp. 57-71.*

* cited by examiner

*Primary Examiner*—Phyllis G. Spivack
(74) *Attorney, Agent, or Firm*—Gilberto M. Villacorta; Steven M. Reid; Foley & Lardner LLP

(57) ABSTRACT

The present invention provides methods for treating social anxiety disorder, comprising administering 2-(7-chloro-1,8-naphthyridin-2-yl)-3-(5-methyl-2-oxo-hexyl)-1-isoindolinone or 2-(7-chloro-1,8-naphthyridine-2-yl)-3-(5-methyl-5-hydroxy-2-oxohexyl)-1-isoindolinone or pharmaceutically acceptable salt, or optical isomer therof, and optionally comprising administering another compound for the treatment of social anxiety disorder that is a GABA agonist.

3 Claims, No Drawings

USE OF PAGOCLONE FOR THE TREATMENT OF SOCIAL ANXIETY DISORDER

CROSS-REFERENCE TO RELATED APPLICATION

This application is a continuation of U.S. patent application Ser. No. 10/133,471, filed Apr. 25, 2002, which claims priority of U.S. Provisional Application No. 60/287,545, filed Apr. 30, 2001.

FIELD OF THE INVENTION

The present invention provides methods, kits and compositions for treating obsessive-compulsive disorder, acute stress disorder, post traumatic stress disorder, social anxiety disorder, somatization disorder, specific social phobia, premenstrual dysphoric disorder, anxiety associated with a medical condition and in particular anxiety associated with Alzheimer's disease, adjustment disorder with anxious mood, dysthymia, specific phobia or fibromyalgia. The present invention also provides compositions, methods and kits comprising a compound of Formula I or a pharmaceutically acceptable salt, optical isomer or prodrug thereof, and an additional compound that is useful to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

BACKGROUND OF THE INVENTION

The compound (+)-2-(7-chloro-1,8-naphthyridine-2-yl)-3-(5-methyl-2-oxo-hexyl)-1-isoindolinone, also called pagoclone, is a GABA (gamma amino butyric acid) receptor ligand that is presently being evaluated in human clinical studies for the treatment of generalized anxiety disorder and panic disorder.

The compound 2-(7-chloro-1,8-naphthyridine-2-yl)-3-(5-methyl-5-hydroxy-2-oxohexyl)-1-isoindolinone is a hydroxy metabolite of pagoclone that shows GABA activity and which can be used to treat generalized anxiety disorder and panic disorder. This compound is disclosed and its preparation and the preparation of each enantiomer is shown in U.S. Pat. No. 5,494,915.

U.S. Pat. No. 4,960,779, issued on Oct. 2, 1990, relates to pyrrole derivatives and compositions comprising pyrrole derivatives, including pagoclone, and to methods of producing an anxiolytic, hypnotic, anticonvulsant, antiepileptic or muscle relaxant therapeutic effect that comprises administering a pyrrole derivative.

The present invention is directed to the use of pyrrole derivatives, and specifically pagoclone or a hydroxy metabolite of pagoclone, 2-(7-chloro-1,8-naphthyridine-2-yl)-3-(5-methyl-5-hydroxy-2-oxohexyl)-1-isoindolinone, to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

GABA is a neurotransmitter that acts at GABA receptors. Two primary types of GABA receptors have been identified as GABM and GABAB. GABAA is a GABA-gated chloride ion channel, whereas GABAB is a G-protein coupled receptor. The present invention is primarily concerned with compounds that act on the GABM receptor.

SUMMARY OF THE INVENTION

The present invention provides methods of treating obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia, the methods comprising administering to a patient in need thereof a therapeutically effective amount of a compound of Formula I

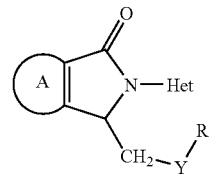

or a pharmaceutically acceptable salt, optical isomer or prodrug thereof, in which A forms with the pyrrole ring an isoindoline ring system;

Het is a naphthyridinyl radical, which is unsubstituted or substituted with a halogen or a (1 to 4C) alkyl, (1 to 4C) alkyloxy, or (1-4C)alkylthio radical;

Y is a CO, C=NOH or CHOH radical; and

R is a straight or branched chain alkenyl radical containing 3 to 10 carbon atoms; a straight or branched unsubstituted alkyl radical of 4 to 10 carbon atoms; an alkyl radical of 4 to 10 carbon atoms that is substituted by hydroxy, alkyloxy, cyclohexyl or dialkylamino; phenyl; or benzyl.

In a preferred embodiment of the methods, the compound is 2-(7-chloro-1,8-naphthyridin-2-yl)-3-(5-methyl-2-oxohexyl)-1-isoindolinone, or a pharmaceutically acceptable salt, optical isomer or prodrug thereof.

In another preferred embodiment of the methods, the compound is (+)-2-(7-chloro-1,8-naphthyridin-2-yl)-3-(5-methyl-2-oxo-hexyl)-1-isoindolinone, or a pharmaceutically acceptable salt or prodrug thereof.

In still another preferred embodiment of the methods, the compound is 2-(7-chloro-1,8-naphthyridine-2-yl)-3-(5-methyl-5-hydroxy-2-oxohexyl)-1-isoindolinone or an optical isomer, pharmaceutically acceptable salt or prodrug thereof.

In another embodiment of the methods, in addition to a compound of Formula I or a pharmaceutically acceptable salt, optical isomer or prodrug thereof, an additional compound useful to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia is administered to the patient.

Also provided by the present invention are kits for use in treating obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia, the kits comprising:

A. a pharmaceutical composition comprising a compound of Formula I

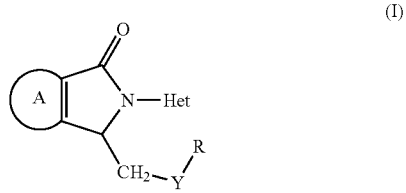

(I)

or a pharmaceutically acceptable salt, optical isomer or prodrug thereof, in which A forms with the pyrrole ring an isoindoline ring system;

Het is a naphthyridinyl radical, which is unsubstituted or substituted with a halogen or a (1 to 4C) alkyl, (1 to 4C) alkyloxy, or (1-4C) alkylthio radical;

Y is a CO, C=NOH or CHOH radical; and

R is a straight or branched chain alkenyl radical containing 3 to 10 carbon atoms; a straight or branched unsubstituted alkyl radical of 4 to 10 carbon atoms; an alkyl radical of 4 to 10 carbon atoms that is substituted by hydroxy alkyloxy, cyclohexyl or dialkylamino; phenyl; or benzyl; and B. instructions for administering the pharmaceutical composition comprising a compound of Formula I or a pharmaceutically acceptable salt, optical isomer or prodrug thereof to a patient in need thereof to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

The present invention also provides pharmaceutical compositions comprising a compound of Formula I or a pharmaceutically acceptable salt, optical isomer or prodrug thereof, and an additional compound that can be used to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

In a preferred embodiment of the pharmaceutical compositions, the compound of Formula I is (+)-2-(7-chloro-1,8-naphthyridin-2-yl)-3-(5-methyl-2-oxo-hexyl)-1-isoindolinone, or a pharmaceutically acceptable salt or prodrug thereof.

In another preferred embodiment of the pharmaceutical compositions, the additional compound is a selective serotonin reuptake inhibitor, a monoamine oxidase inhibitor or an anxiolytic.

DETAILED DESCRIPTION OF THE INVENTION

The present invention provides methods of treating obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia, the methods comprising administering to a patient in need thereof a therapeutically effective amount of a compound that is a GABAA ligand. Preferably, the compound is a GABAA agonist, and more preferably, a GABAA partial agonist. Most preferably, the compound is a compound of Formula I

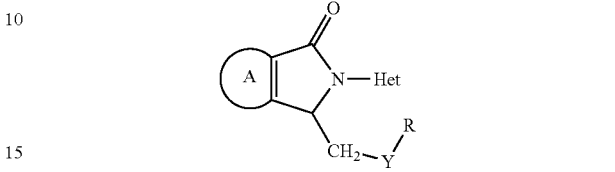

(I)

or a pharmaceutically acceptable salt, optical isomer or prodrug thereof, in which A forms with the pyrrole ring an isoindoline ring system;

Het is a naphthyridinyl radical, which is unsubstituted or substituted with a halogen or a (1 to 4C) alkyl, (1 to 4C) alkyloxy, or (1-4C)alkylthio radical;

Y is a CO, C=NOH or CHOH radical; and

R is a straight or branched chain alkenyl radical containing 3 to 10 carbon atoms; a straight or branched unsubstituted alkyl radical of 4 to 10 carbon atoms; an alkyl radical of 4 to 10 carbon atoms that is substituted by hydroxy, alkyloxy, cyclohexyl or dialkylamino; phenyl; or benzyl.

The compounds of Formula I can also be used to treat depression, anxiety, panic attacks, hiccups, attention deficit disorder, bipolar disorder, intermittent explosive disorder, eating disorders such as anorexia and bulimia, borderline personality disorders, or Parkinson's disease. The compounds of Formula I are also useful as appetite suppressants, to help in smoking cessation, to treat substance withdrawal, such as alcohol withdrawal, and to treat extra pyramidal symptoms.

In a preferred embodiment, the compound of Formula I is (+)-2-(7-chloro-1,8-naphthyridine-2-yl)-3-(5-methyl-2-oxo-hexyl)-1-isoindolinone. In another preferred embodiment, the compound of Formula I is 2-(7-chloro-1,8-naphthyridine-2-yl)-3-(5-methyl-2-oxo-5-hexen-1-yl)-isoindolinone or an optical isomer, pharmaceutically acceptable salt, prodrug, or salt of the prodrug. In another preferred embodiment, the compound of Formula I is 2-(7-chloro-1,8-naphthyridine-2-yl)-3-(5-methyl-5-hydroxy-2-oxohexyl)-1-isoindolinone or an optical isomer, pharmaceutically acceptable salt, or prodrug, or salt of the prodrug.

Also provided by the present invention are kits that comprise a pharmaceutical composition comprising a compound of Formula I or a pharmaceutically acceptable salt, optical isomer or prodrug thereof, and instructions for administering the pharmaceutical composition to a patient in need thereof to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

In another aspect, the present invention provides pharmaceutical compositions comprising a compound of Formula I or a pharmaceutically acceptable salt, optical isomer or prodrug thereof, and one or more additional compounds useful to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

The present invention further provides pharmaceutical compositions that comprise a compound of Formula I or a pharmaceutically acceptable salt, optical isomer or prodrug thereof, and one or more compounds useful to treat depression, anxiety, panic attacks, hiccups, attention deficit disorder, bipolar disorder, intermittent explosive disorder, eating disorders such as anorexia and bulimia, borderline personality disorders, and Parkinson's disease. The compounds of Formula I can also be used in combination with other compounds that are useful as appetite suppressants, to help in smoking cessation, to treat substance withdrawal, such as alcohol withdrawal, and to treat extra pyramidal symptoms.

In another aspect, the present invention provides kits that comprise a pharmaceutical composition comprising a compound of Formula I or an optical isomer, pharmaceutically acceptable salt or prodrug thereof and an additional compound that is useful to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

Obsessive-compulsive disorder is characterized by recurrent, unwanted, intrusive ideas, images or impulses and an urge to do something to lessen the discomfort caused by the ideas, images or impulses. Present treatments include the selective serotonin reuptake inhibitors (SSRIs) such as fluoxetine, fluvoxamine, paroxetine and sertraline. Clomipramine and other tricyclic antidepressants have also been used.

Post traumatic stress disorder occurs when a patient reexperiences a traumatic event that has occurred, which reexperience causes intense fear, helplessness, horror and results in the avoidance of stimuli associated with the trauma. Present treatments for post traumatic stress disorder include antidepressants such as SSRIs or monoamine oxidase inhibitors, or anxiolytics.

Social anxiety disorder is also called social phobia and is characterized by anxiety resulting from social situations or performance based situations. A patient having social anxiety disorder is uncomfortable in social situations in general and may avoid social situations to reduce the associated anxiety.

Somatization disorder is a chronic, severe psychiatric disorder characterized by many recurring clinically significant complaints, including pain or gastrointestinal, sexual or neurological symptoms that cannot be explained by a physical disorder.

Specific social phobia is a disorder in which a patient avoids a specific social situation. This disorder can be contrasted with social anxiety disorder because the patient's anxiety can be attributed to a specific social or performance based situation, rather than social or performance based situations in general. For example, the patient may be uncharacteristically anxious about public speaking.

Premenstrual dysphoric disorder is characterized by severe mood swings and physical symptoms that interfere with everyday life, including interfering with relationships with friends and family. Typically, the symptoms appear about a week before and end about a few days after the onset of menstruation. Premenstrual dysphoric disorder can include a combination of symptoms such as irritability, depressed mood, anxiety, sleep disturbance, difficulty concentrating, angry outbursts, breast tenderness or bloating. Treatment of premenstrual dysphoric disorder includes the use of SSRIs.

Anxiety associated with a medical condition is a clinically significant anxiety that is judged to be due to a medical condition. An example of a medical condition that can cause anxiety is Alzheimer's disease. Examples of other medical conditions that cause anxiety include AIDS/HIV and cancer.

Adjustment disorder with anxious mood is a type of anxiety, which unlike post traumatic stress disorder that results from an extreme stimuli, results from less extreme stimuli. The emotional or behavioral symptoms usually are in response to an identifiable psychosocial stressor.

Dysthymia, also known as dysthymic disorder, is a form of depression that typically begins in childhood or adolescence. The patient may be mildly depressed for a long period of time with more severe depressions also presenting during the time period. A patient having dysthymia can be habitually gloomy, pessimistic, humorless or incapable of fun. The patient can also be passive, lethargic, introverted, skeptical, hypercritical or complaining, and may be self-critical, self-reproaching, self-derogatory and preoccupied with inadequacy, failure or negative events. SSRIs are the favored treatment, but tricyclic antidepressants and monoamine oxidase inhibitors have also been used to treat dysthymia.

Specific phobia is an excessive or unreasonable fear, without apparent justification, of a specific place, thing or situation, for example a fear of blood, crowds, dogs, snakes, heights, riding public transportation, driving a car, flying, thunderstorms, water, etc. Typically, an adult patient recognizes that the fear is excessive or unreasonable, but children may not recognize this.

Fibromyalgia is a group of nonarticular disorders characterized by achy pain, tenderness and stiffness of muscles, areas of tendon insertions, and adjacent soft tissue structures. The disorders that comprise fibromyalgia include myofascial pain syndrome, fibrositis, and fibromyositis. Fibromyalgia has been treated using tricyclic antidepressants, nonsteroidal anti-inflammatory compounds (NSAIDs) and SSRIs.

The disorders and conditions above are well known to those skilled on the art. Methods of diagnosing and a description of these conditions can be found in *Diagnostic And Statistical Manual of Mental Disorders*, Fourth Edition, American Psychiatric Association, Washington, D.C., 1994.

Preferred compounds of the methods, kits and compositions of the present invention include compounds of Formula I

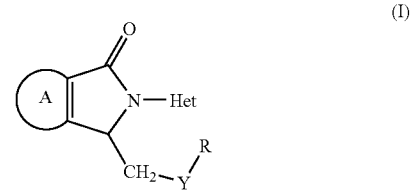

or pharmaceutically acceptable salts, optical isomers or prodrugs thereof, in which A forms with the pyrrole ring an isoindoline ring system;

Het is a naphthyridinyl radical, which is unsubstituted or substituted with a halogen or a (1 to 4C) alkyl, (1 to 4C) alkyloxy, or (1-4C)alkylthio radical;

Y is a CO, C=NOH or CHOH radical; and

R is a straight or branched chain alkenyl radical containing 3 to 10 carbon atoms; a straight or branched unsubstituted alkyl radical of 4 to 10 carbon atoms; an alkyl radical of 4 to 10 carbon atoms that is substituted by hydroxy, alkyloxy, cyclohexyl or dialkylamino; phenyl; or benzyl.

A preferred compound of Formula I is 2-(7-chloro-1,8-naphthyridin-2-yl)-3-(5-methyl-2-oxo-hexyl)-1-isoindolinone, or a pharmaceutically acceptable salt, optical isomer or prodrug thereof. A more preferred compound of Formula I is (+)-2-(7-chloro-1,8-naphthyridin-2-yl)-3-(5-methyl-2-oxohexyl)-1-isoindolinone, or a pharmaceutically acceptable salt or prodrug thereof. Another compound of Formula I that can be used in the present invention is 2-(7-chloro-1,8-naphthyridin-2-yl)-3-(5-methyl-5-hydroxy-2-oxohexyl)-1-isoindolinone or an optical isomer, pharmaceutically acceptable salt or prodrug thereof.

The terms "treat", "treatment", and "treating" include preventative (e.g., prophylactic) and palliative treatment or the act of providing preventative or palliative treatment.

The term "patient" means animals, particularly mammals. Preferred patients are humans.

The phrase "a patient in need thereof" is a patient who has or is at risk of having a condition as described herein.

The expression "pharmaceutically acceptable salts" includes both pharmaceutically acceptable acid addition salts and pharmaceutically acceptable cationic salts. The expression "pharmaceutically-acceptable cationic salts" is intended to include, but is not limited to, such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to include, but is not limited to, such salts as the hydrochloride, hydrobromide, sulfate, hydrogen sulfate, phosphate, hydrogen phosphate, dihydrogenphosphate, acetate, succinate, tartrate, citrate, methanesulfonate (mesylate) and p-toluenesulfonate (tosylate) salts.

The pharmaceutically acceptable acid addition salts of the compounds of this invention may be formed of the compound itself, or of any of its esters, and include the pharmaceutically acceptable salts that are often used in pharmaceutical chemistry. For example, salts may be formed with inorganic or organic acids such as hydrochloric acid, hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferably with hydrochloric acid, citric acid, benzoic acid, maleic acid, acetic acid or propionic acid.

The salts of basic compounds can be formed by reacting the compound with a suitable acid. The salts are typically formed in high yields at moderate temperatures, and often are prepared by isolating the compound from a suitable acidic wash as the final step of the synthesis. The salt-forming acid is dissolved in an appropriate organic solvent, or aqueous organic solvent, such as an alkanol, ketone or ester. On the other hand, if a compound is desired in the free base form, it can be isolated from a basic final wash step. A preferred technique for preparing hydrochlorides is to dissolve the free base in a suitable solvent and dry the solution thoroughly, as over molecular sieves, before bubbling hydrogen chloride gas through it. It will also be recognized that it is possible to administer amorphous forms of the compounds.

One of ordinary skill in the art will recognize that certain compounds of this invention will contain one or more atoms which may be in a particular stereochemical, tautomeric, or geometric configuration, giving rise to stereoisomers, tautomers and configurational isomers. All such tautomers and isomers and mixtures thereof are included in this invention. Hydrates and solvates of the compounds of this invention are also included.

The subject invention also includes isotopically-labeled compounds, which are structurally identical to those disclosed above, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}$, $^{17}O$, $^{31}P$, $^{32}P$, $^{35}S$, $^{18}F$ and $^{36}Cl$, respectively. Compounds of the present invention, prodrugs thereof, and pharmaceutically acceptable salts of said compounds and of said prodrugs which contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of this invention and prodrugs thereof can generally be prepared by carrying out known or referenced procedures and by substituting a readily available isotopically labeled reagent for a non-isotopically labeled reagent.

Those of ordinary skill in the art will recognize that physiologically active compounds which have accessible hydroxy groups can be administered in the form of pharmaceutically acceptable esters. The compounds of this invention can be effectively administered as an ester, formed on the hydroxy groups. It is possible to adjust the rate or duration of action of the compound by appropriate choices of ester groups.

The term "prodrug" means a compound that is transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the *A.C.S. Symposium Series*, and in *Bioreversible Carriers in Drug Design*, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy) ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as α-dimethylaminoethyl), carbamoyl-($C_1$-$C_2$)alkyl, N,N-di($C_1$-$C_2$)alkylcarbamoyl-($C_1$-$C_2$)alkyl or piperidino-, pyrrolidino- or morpholino($C_2$-$C_3$)alkyl.

Similarly, if a compound of the present invention comprises an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanoyl, arylacyl, or α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a compound of the present invention comprises an amine functional group, a prodrug can be formed by the replacement of a hydrogen atom in the amine group with a group such as $R^X$-carbonyl, $R^X$O-carbonyl, $NR^XR^{X'}$-carbonyl where $R^X$ and $R^{X'}$ are each independently $(C_1-C_{10})$alkyl, $(C_3-C_7)$cycloalkyl, benzyl, or $R^X$-carbonyl is a natural α-aminoacyl or natural α-aminoacyl-natural α-aminoacyl, —C(OH)C(O)O$Y^X$ wherein $Y^X$ is H, $(C_1-C_6)$alkyl or benzyl, —C(O$Y^{X0}$) $Y^{X1}$ wherein $Y^{X0}$ is $(C_1-C_4)$ alkyl and $Y^{X1}$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, or —C($Y^{X2}$) $Y^{X3}$ wherein $Y^{X2}$ is H or methyl and $Y^{X3}$ is mono-N— or di-N,N—$(C_1-C_6)$alkylamino, morpholino, piperidin-1-yl or pyrrolidin-1-yl.

As used herein, the term "effective amount" means an amount of compound that is capable of treating the described conditions. The specific dose of a compound administered according to this invention will, of course, be determined by the particular circumstances surrounding the case including, for example, the compound administered, the route of administration and the severity of the condition being treated.

The dose of a compound of this invention to be administered to a subject is rather widely variable and subject to the judgement of the attending physician. It should be noted that it may be necessary to adjust the dose of a compound when it is administered in the form of a salt, such as a laureate, the salt forming moiety of which has an appreciable molecular weight.

The following dosage amounts are for an average human subject having a weight of about 65 kg to about 70 kg. One skilled in the art will readily be able to determine the dosage amount required for a subject whose weight falls outside the 65 kg to 70 kg range, based upon the medical history of the subject. All doses set forth herein are daily doses of the free base or acid forms. Calculation of the dosage amount for other forms of the free base or acid forms such as salts or hydrates is easily accomplished by performing a simple ratio relative to the molecular weights of the species involved.

The general range of effective administration rates of the compounds of Formula I is from about 0.01 mg/day to about 20 mg/day. A preferred dosage range is from about 0.05 mg/day to about 5.0 mg/day. A more preferred range in about 0.3 mg/day to about 1.2 mg/day. Of course, it is often practical to administer the daily dose of a compound in portions, at various hours of the day. However, in any given case, the amount of compound administered will depend on such factors as the potency of the specific compound, the solubility of the compound, the formulation used and the route of administration.

The following paragraphs describe exemplary formulations, dosages etc. useful for non-human animals. The administration of a compound of the present invention can be effected orally or non-orally, for example by injection. An amount of a compound is administered such that an effective dose is received, generally a daily dose which, when administered orally to an animal is usually between about 0.01 and about 100 mg/kg of body weight, preferably between about 0.1 and about 50 mg/kg of body weight. Conveniently, the medication can be carried in the drinking water so that a therapeutic dosage of the agent is ingested with the daily water supply. The agent can be directly metered into drinking water, preferably in the form of a liquid, water-soluble concentrate (such as an aqueous solution of a water soluble salt). Conveniently, the active ingredient can also be added directly to the feed, as such, or in the form of an animal feed supplement, also referred to as a premix or concentrate. A premix or concentrate of a therapeutic agent in a carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the active materials in the finished feed with which the premix is blended. It is important that the compound be thoroughly blended into the premix and, subsequently, the feed. In this respect, the agent may be dispersed or dissolved in a suitable oily vehicle such as soybean oil, corn oil, cottonseed oil, and the like, or in a volatile organic solvent and then blended with the carrier. It will be appreciated that the proportions of active material in the concentrate are capable of wide variation since the amount of agent in the finished feed may be adjusted by blending the appropriate proportion of premix with the feed to obtain a desired level of therapeutic agent.

High potency concentrates may be blended by the feed manufacturer with a proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound according to the invention. The mixtures are thoroughly blended by standard procedures, such as in a twin shell blender, to ensure homogeneity.

If the supplement is used as a top dressing for the feed, it likewise helps to ensure uniformity of distribution of the active material across the top of the dressed feed.

Paste formulations can be prepared by dispersing the active compound in a pharmaceutically acceptable oil such as peanut oil, sesame oil, corn oil, or the like.

Pellets containing an effective amount of a compound of Formula I can be prepared by admixing a compound of Formula I with a diluent such as carbowax, carnauba wax, and the like, and a lubricant, such as magnesium or calcium stearate, can be added to improve the pelleting process.

It is recognized that more than one pellet may be administered to an animal to achieve the desired dose level. Moreover, it has been found that implants may also be made periodically during the animal treatment period in order to maintain the proper active agent in the level animal's body.

Methods of formulation are well known in the art and are disclosed, for example, in *Remington: The Science and Practice of Pharmacy*, Alphonso R. Genaro, Mack Publishing Company, Easton, Pa., 19th Edition (1995). Pharmaceutical compositions for use within the present invention can be in the form of sterile, non-pyrogenic liquid solutions or suspensions, coated capsules, suppositories, lyophilized powders, transdermal patches or other forms known in the art.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant may be necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances that facilitate the disintegration of a tablet to release a compound when the tablet becomes wet. They include starches, clays, celluloses, algins and gums, more particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavorant and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may also include making pellets of several different dissolution rates and filling capsules with a mixture of the pellets. Tablets or capsules may be coated with a film which resists dissolution for a predictable period of time. Topical formulations may be designed to yield delayed and/or prolonged percutaneous absorption of a compound. Even the parenteral preparations may be made long-acting, by dissolving or suspending the compound in oily or emulsified vehicles which allow it to disperse slowly in the serum.

The present invention also provides kits for use to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

The kits comprise: A) a pharmaceutical composition comprising a compound of Formula I or a pharmaceutically acceptable salt, optical isomer or prodrug thereof; and B) instructions describing a method of using the pharmaceutical composition to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia. In preferred kits, the compound is (+)-2-(7-chloro-1,8-naphthyridin-2-yl)-3-(5-methyl-2-oxo-hexyl)-1-isoindolinone, or a pharmaceutically acceptable salt or prodrug thereof, or 2-(7-chloro-1,8-naphthyridine-2-yl)-3-(5-methyl-5-hydroxy-2-oxohexyl)-1-isoindolinone or an optical isomer, pharmaceutically acceptable salt, or prodrug, or salt of the prodrug.

Also provided by the present invention are kits that comprise a pharmaceutical composition comprising a compound of Formula I or an optical isomer, pharmaceutically acceptable salt or prodrug thereof, and an additional compound that is useful to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

A "kit" as used in the instant application includes a container for containing the pharmaceutical compositions and may also include divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is. a calendar printed on the card e.g., as follows "First Week, Monday, Tuesday,"... etc ... "Second Week, Monday, Tuesday,..." etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The kits, methods and compositions of the present invention may also include, in addition to a compound of Formula I or a pharmaceutically acceptable salt, optical isomer or prodrug thereof, one or more additional pharmaceutically active compounds that can be use to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia. Preferably, any additional compound is a GABAA receptor ligand or another compound that is useful to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia. In addition, the compounds of Formula I or a pharmaceutically acceptable salt, optical isomer or prodrug thereof can be used in combination with one or more additional compounds of Formula I or a pharmaceutically acceptable salt, optical isomer or prodrug thereof. The compounds of Formula I or a pharmaceutically acceptable salt, optical isomer or prodrug thereof can also be used in combination with compounds that are useful to treat depression, anxiety, panic attacks, hiccups, attention deficit disorder, bipolar disorder, intermittent explosive disorder, eating disorders such as anorexia and bulimia, borderline personality disorders, and Parkinson's disease. The compounds of Formula I can also be used in combination with other compounds that are useful as appetite suppressants, to help in smoking cessation, to treat substance withdrawal, such as alcohol withdrawal, and to treat extra pyramidal symptoms.

Any GABA agonist may be used as an additional compound in the methods, compositions and kits of the present invention. The activity of GABA agonists may readily be determined by methods known to those skilled in the art, including the procedures disclosed in Janssens de Verebeke, P et al., Biochem. Pharmacol., 31, 2257-2261 (1982), Loscher, W., Biochem. Pharmacol., 31, 837-842, (1982) and/or Phillips, N. et al., Biochem. Pharmacol., 31, 2257-2261.

Preferred GABA agonists, which may be prepared by procedures available in the art, include: muscimol, progabide, riluzole, baclofen, gabapentin (Neurontin®), vigabatrin, valproic acid, tiagabine (Gabitril®), lamotrigine (Lamictal®), pregabalin, phenytoin (Dilantin®), carbamazepine (Tegretol®), topiramate (Topamax®), or N-{[3-fluoro-4-(2-propylaminoethoxy)]phenyl}-4-oxo-4,5,6,7-tetrahydro-1H-indole-3-carboxamide, or optical isomers, prodrugs or pharmaceutically acceptable salts of those GABA agonists. Other GABA agonists that can be used in the methods, kits and compositions of the present invention included those disclosed in WO 01/14337, which are selective ligands for GABAA receptors, with high binding affinity for the alpha 2 and/or alpha 3 subunits.

Compounds that are used to treat depression and which can be used in combination with the compounds of Formula I or a pharmaceutically acceptable salt, optical isomer or prodrug thereof in the present methods, compositions and kits include selective serotonin reuptake inhibitors (SSRIs) such as citalopram (Celexa®), paroxetine (Paxil®), fluoxetine (Prozac®), and sertraline hydrochloride (Zoloft®) fluvoxamine (Luvox®); tricylclic compounds such as amitriptyline (Elvanil®), perphenazine and amitriptyline (Etrafon®), imipramine (Tofranil®), chlordiazepoxide and amitriptyline (Limbitrol®), desipramine (Norpramin®), doxepin (Sinequan®), trimipramine (Surmontil®) and protriptyline (Vivactil®); monoamine oxidase inhibitors such as pheneizine (Nardil®) and tranylcypromine (Parnate®); and other compounds that are used to treat depression such as venlafaxine (Effexor®), mirtazapine (Remeron®), nefazodone (Serzone®) and bupropion (Wellbutrin®). A preferred combination is pagoclone and sertraline hydrochlorde.

Compounds that are used to treat anxiety and which can be used in combination with the compounds of Formula I or a pharmaceutically acceptable salt, optical isomer or prodrug thereof in the present methods, kits and compositions include bezodiazepines such as lorazepam (Ativan®), chlordiazepoxide (Librium®), chlordiazepoxide and amitriptyline (Limbitrol®), clorazepate (Tranxene®), diazepam (Valium®) and alprazolam (Xanax®). Other antianxiety agents that can be used in combination include hydroxyzine (Atarax®), buspirone (BuSpar®), venlafaxin (Effexor®), mephobarbital (Mebaral®), Miltown®, paroxetine (Paxil®), doxepin (Sinequan®), perphenazine and amitriptyline (Triavil®), clonazepam (klonopin®), ozazepam (Serax®) and hydroxyzine (Vistaril®).

Compounds that are used to treat panic attacks and which can be used in combination with a compound of Formula I or a pharmaceutically acceptable salt, optical isomer or prodrug thereof in the present methods, kits and compositions include clonazepam (Klonopin®), paroxetine (Paxil®), alprazolam (Xanax®) and sertraline hydrochloride (Zoloft®).

Preferred combinations of compounds of Formula I or a pharmaceutically acceptable salt, optical isomer or prodrug thereof, including pagoclone, include combinations with gabapentin, pregabalin, phenytoin, sertaline, phenelzine, hydroxyzine and doxepin. It is also possible to administer the compounds of Formula I or a pharmaceutically acceptable salt, optical isomer or prodrug thereof in combination with compounds such as donepezil, tacrine, and celecoxib. The combination of a compound of Formula I or a pharmaceutically acceptable salt, optical isomer or prodrug thereof, and donepezil hydrochloride or tacrine hydrochloride is particularly contemplated in the treatment of anxiety associated with Alzheimer's disease. The combination of a compound of Formula I or a pharmaceutically acceptable salt, optical isomer or prodrug thereof with a selective COX-2 inhibitors is preferred in the treatment of fibromyalgia.

The compounds of Formula I can also be used in combination with other compounds that can be used to treat schizophrenia such as ziprasidone (Geodon®) or olanzapine (Zyprexa®).

The compounds of Formula I can also be used in combination with compounds that can be used to treat erectile dysfunction such as sildenafil citrate (Viagra®) or other PDE5 ligands. The compounds of Formula can also be used in combination with IC351 (Cialis™) or vardenafil.

The compounds of the present invention can also be used in combination with antipsychotics such as risperidone (Risperdal®).

The compounds of Formula I can also be used in combination with compounds that are used to help in smoking cessation such as bupropion (Zyban®), 6,10-methano-6H-pyrazino[2,3-h][3]benzapine, 7,8,9,10-tetrqhydro-(CAS Registry Number 249296) or a pharmaceutically acceptable salt or prodrug thereof, or nicotine delivery systems such as Nicorrette® gum, Nicotrol® Inhaler, or Nicotrol® Patch.

The compounds of Formula I can also be used in combination with norepinephrine reuptake inhibitors, such as reboxetine, benzodiazpines or a NK1 antagonists.

The compounds of Formula I can also be used in combination with compounds that are used to treat specific phobia such as lorazepam (Ativan®), buspirone (BuSpar®), mepabromate (Equanil® or Miltown®), propanolol (Inderal®), clonazepam (Klonopin®), chlordiazepoxide (Librium®), fluvoxamine (Luvox®), paroxetine (Paxil®), oxazepam (Serax®), clorazepate disodium (Tranxene®), diazepam (Valium®), midazolam hydrochloride (Versed®), or alprazolam (Xanax®).

The commercial products noted above may be a particular salt or prodrug of the active compound. For example, Zoloft® is the hydrochloride salt of the active compound sertraline. It is intended that the present invention include salts and prodrugs of active compounds. Thus, when the tradename (e.g., sertraline) or trademark (e.g., Zoloft®) is used, it is intended to mean the active compound or a pharmaceutically acceptable salt or prodrug thereof.

It is also noted that pagoclone can be used in combination with 2-(7-chloro-1,8-naphthyridine-2-yl)-3-(5-methyl-5-hydroxy-2-oxohexyl)-1-isoindolinone or an optical isomer, pharmaceutically acceptable salt or prodrug thereof.

In the combination aspect of the methods, compositions and kits of the present invention, the compound of Formula I or a pharmaceutically acceptable salt, optical isomer or prodrug thereof, and any additional compounds, can be administered in the same dosage form or in separate dosage forms. The dosage forms can be the same (e.g., both tablets) or different. Likewise, the compounds can be administered at the same time or at different times. All variations are intended to be included in the present methods and kits.

All documents cited herein, including patents and patent applications, are hereby incorporated by reference.

What is claimed is:

1. A method of treating social anxiety disorder, comprising:
    administering to a patient in need thereof a therapeutically effective amount of a compound of 2-(7-chloro-1,8-naphthyridin-2-yl)-3-(5-methyl-2-oxo-hexyl)-1-isoindolinone or 2-(7-chloro- 1,8-naphthyridine-2-yl)-3-(5-methyl-5-hydroxy-2-oxohexyl)-1-isoindolinone, or a pharmaceutically acceptable salt thereof.

2. The method of claim 1, wherein the compound is (+)-2-(7-chloro -1 ,8-naphthyridin-2-yl)-3-(5-methyl-2-oxo-hexyl)-1-isoindolinone, or a pharmaceutically acceptable salt thereof.

3. The method of claim 1, further comprising administering another compound for the treatment of social anxiety disorder, which is a GABA agonist.

* * * * *